United States Patent [19]

Moore

[11] Patent Number: 5,332,548
[45] Date of Patent: Jul. 26, 1994

[54] ANALYTICAL DEVICE AND METHOD OF USING SAME

[76] Inventor: Robert E. Moore, 2865 Danbe Rd., Oshkosh, Wis. 54904

[21] Appl. No.: 814,720

[22] Filed: Dec. 30, 1991

[51] Int. Cl.$^5$ ............................................. G01N 31/22
[52] U.S. Cl. ....................... 422/56; 422/87; 422/61; 436/3; 436/130; 436/169
[58] Field of Search ........................... 422/56–58, 422/86, 87, 61; 436/3, 130, 167, 169, 181

[56] References Cited

U.S. PATENT DOCUMENTS

| | | | |
|---|---|---|---|
| 3,830,094 | 8/1974 | Leger | 436/130 X |
| 3,945,798 | 3/1976 | Young | 436/130 |
| 4,380,587 | 4/1983 | Koocher | 436/128 |
| 4,511,658 | 4/1985 | Lambert et al. | 436/130 |
| 5,096,813 | 3/1992 | Krumhar et al. | 422/57 X |

*Primary Examiner*—Jill A. Johnston
*Attorney, Agent, or Firm*—R. Jonathan Peters

[57] ABSTRACT

The invention provides an analytical device, and method of using same, for detecting a gaseous or volatile analyte and adaptable to be applied directly to the surface of a solid material from which said analyte is emitted. The device comprises a substrate for disposition adjacent a surface of the solid material, and applied to the substrate are (a) an analyte-reactive component which reacts with said analyte, and (b) an indicator in sufficient quantity to produce a detectable signal selective to the reaction thereby detecting said analyte. The analytical device has no exogenous reagent.

36 Claims, 3 Drawing Sheets

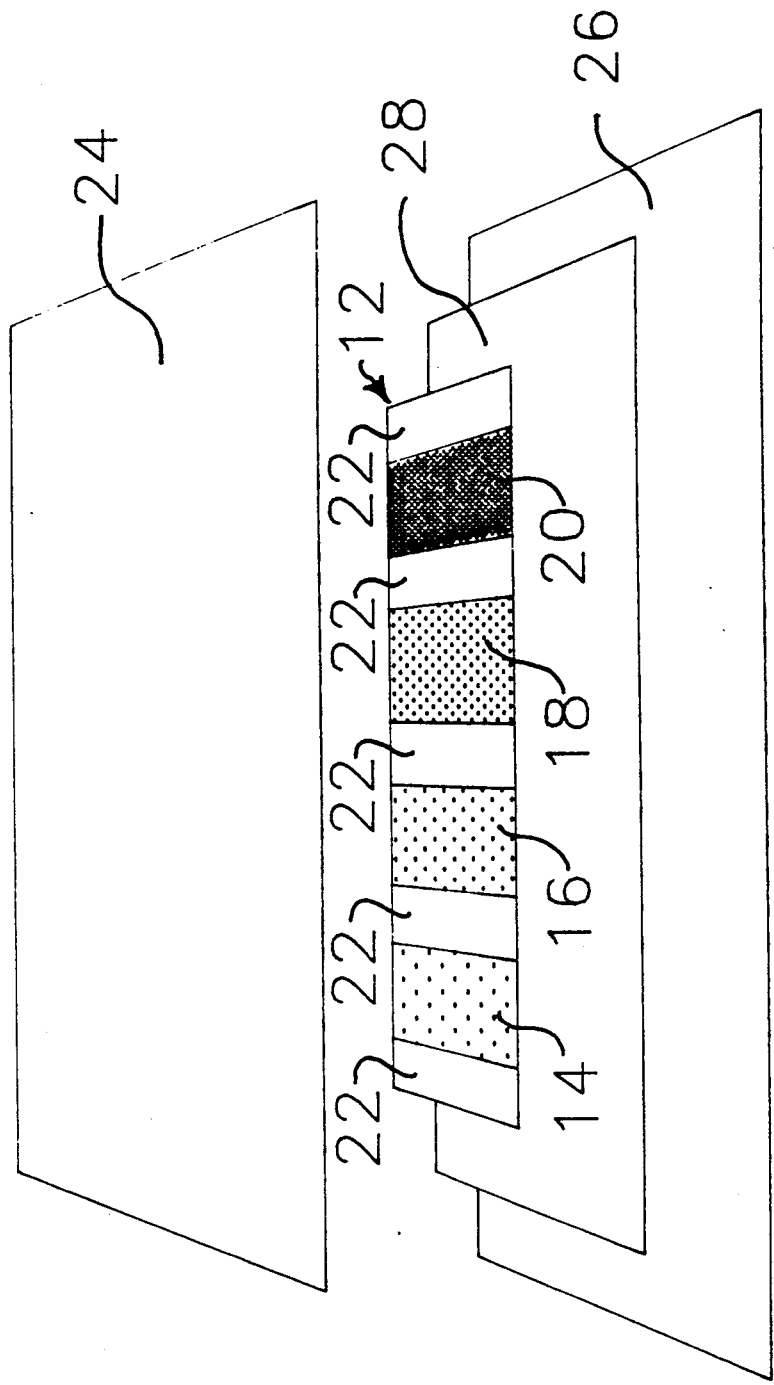

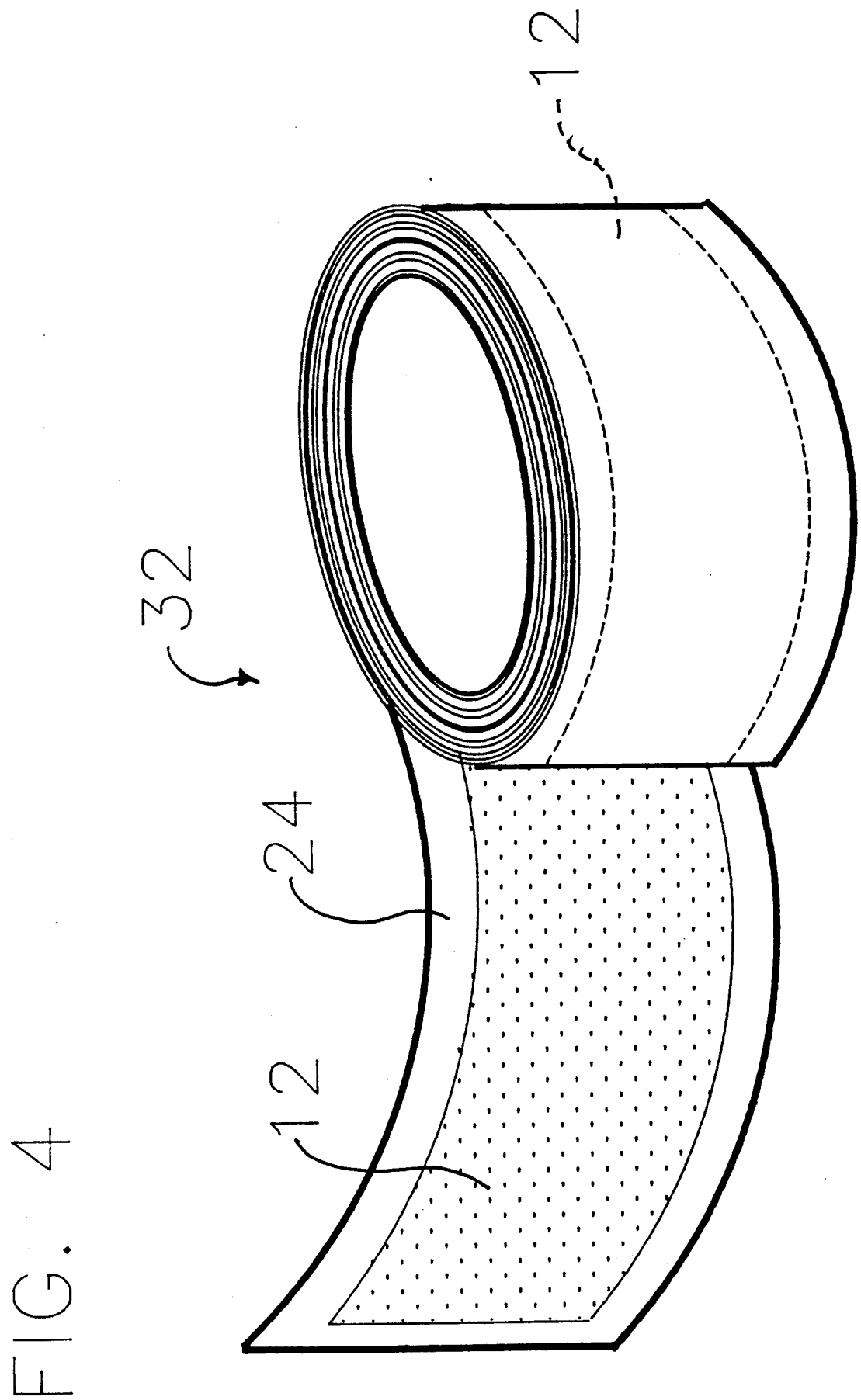

ANALYTICAL DEVICE AND METHOD OF USING SAME

Field of the Invention

This invention relates to an analytical device for detecting a gaseous or volatile analyte emitted from a solid material. In a more specific aspect, this invention relates to an analytical device adaptable to be applied directly to the surface of a solid material for detecting a gaseous or volatile analyte emitted from the solid material, and to the method of using the analytical element in detecting the gaseous or volatile analyte emissions from a solid material.

BACKGROUND OF THE INVENTION AND PRIOR ART

A large number of organic compounds that can be potentially toxic are used extensively in a wide variety of materials or products. Representative examples of such materials include particle board, plywood, furniture, cabinets, and textiles containing a synthetic resin adhesive such as formaldehyde or a derivative thereof; urea formaldehyde foam insulation; paper products impregnated with wet strength agents; resins, adhesives, paints, varnishes, and the like, containing aliphatic and aromatic hydrocarbons, alcohols, ketones, and esters as vehicles, thinners, or solvents. These organic compounds fulfill a need, and therefore usage is expansive and commonplace. However, many such organic compounds used in the manufacture of these materials are volatile and emit antigenic or noxious fumes. Numerous precautions or safety standards have been implemented by industry to identify the sources of the volatile fumes, to control the exposure of the worker to these fumes, and to prevent the ingestion or inhalation of these fumes by the worker. However, it is not uncommon that after the installation of these materials or products in the house, office, or work area, volatile or gaseous organics continue to be emitted or released from the materials or products to the atmosphere of such an enclosed environment, which even occurs with materials bearing a surface treatment. Many of these gasses have known toxic characteristics, and can cause irritation to the skin, eyes, nose or throat, or cause headaches, drowsiness or digestive disorders. Although the problem is most severe with newly manufactured materials or products, the problem may be latent, and this noxious effect can be long-term and persist for several years after the manufacture and installation of the material.

This latent problem and lingering noxious effect exists, for example, in the case of formaldehyde typically used as an adhesive or as a resin component in wood products, and is known to manifest itself for as long as seven years following manufacture and installation. Formaldehyde is one of the world's most important industrial chemicals having a reported annual production of about 12 million metric tons. Wood products account for a large percentage of the total formaldehyde demand, and consequently these health and environmental problems with indoor air have become particularly aggravated. In fact, it is reported that most people in the industrialized nations spend up to about 90 percent of their time indoors, and therefore it is essential to provide a safe environment for the occupants. A number of U.S. governmental agencies have issued or are proposing to issue regulations limiting permissible amounts of formaldehyde emissions from various products and materials. For example, Department of Housing and Urban Development (HUD) has implemented such standards for particle board and plywood, as found in 24 CFR 3280.308 et seq. According to these standards, product certification is required by testing in a large scale test chamber, which may be augmented by more frequent small scale testing to monitor during production. The small scale testing, e.g., the two hour desiccator test, utilizes small samples cut from a large scale production line panel or board. The samples are first preconditioned by sealing the edges with paraffin, and then placed in a desiccator for vapor phase extraction of formaldehyde gas into distilled water. The solution is then analyzed by wet chemistry to determine the gaseous emissions. Additionally, the Science Advisory Board has assisted the Occupational and Safety Health Administration in providing standards for noxious emissions, including standard for formaldehyde emissions (see 29 CFR 1910, Occupational Exposure to Formaldehyde).

Other analytical devices have been developed for the purpose of detecting and monitoring gaseous or volatile toxins existing in an indoor environment, but these devices either require wet chemical analysis, such as the two hour desiccator test described above, or are limited to monitoring ambient or atmospheric air. For example, aqueous and solid media have been used for collecting formaldehyde from air samples, as reported by Matthews et al., "Solid Sorbent for Formaldehyde Monitoring", Analytical Chemistry, Vol. 54, No. 9, pp 1495–1498, August 1982, which utilizes 13X molecular sieve as a sorbent media; and by Liparl et al., "2,4-Dinitrophenylhydrazine-Coated Florisil Sampling Cartridges for the Determination of Formaldehyde in Air", Environ. Sci. Technol., Vol. 19, No. 1, pp 70–74, 1985, which utilizes Florisil (magnesium silicate) coated with 2,4-DNPH. Most of the techniques of this type, however, monitor ambient air only, and cannot be used for detecting a gaseous emission from a particular building material or product. However, the monitoring method of Matthews et al. has been used for determining gas emitted from a solid material, but this method and other similar methods require additional steps involving wet analysis to complete the sampling, in that the reaction product is eluted from the sorbent media and then analyzed by chromatography or spectrophotometry.

Thus, these techniques monitor the formaldehyde after it has escaped from the source and blended with the surrounding air, and therefore do not identify the source of the emissions; or, in the case of Matthews et al., cited above, for monitoring emissions from a solid material, the formaldehyde is first collected as emitted from the source, the formaldehyde eluted from the sorbent, and then in a separate step analyzed by wet chemistry.

A more simple technique utilizing a colorimetric detector for detecting formaldehyde in air is disclosed in U.S. Pat. No. 4,511,658 to Lambert et al. According to this patent, an inert support, such as filter paper or a granular absorbent, is coated with 4-amino-3-hydrazino-5-mercapto-1,2,4-triazole, a ketone such as acetone, and a metal bicarbonate such as sodium bicarbonate. Formaldehyde in the air sample enters into the reaction chain, and in the presence of moisture (i.e., water), produces the chromophore having a purple color. Although the detector is simple and requires visual observation only for a color change, the device is limited to detecting formaldehyde in ambient or atmospheric air, and, most significantly, requires the presence of water as an exogenous reagent.

Tests strips comprising an inert substrate or carrier, such as paper or film, and impregnated with testing reagents that produce a visible color change are well known in the art. Soviet Union Patent 0728083, Apr. 15, 1980, discloses a strip indicator for determining acetone in air using moist tape impregnated with hydroxylamine hydrochloride and Bromophenol Blue, and assessed by photocolorimetry. Additional art disclosing detectors of this type include U.S. Pat. No. 3,443,903 to Heidelberg et al.; 4,427,632 to Okaniwa et al.; 3,043,669 to Charles; 4,558,012 to Nygen et al.; and 4,592,893 to Poppe. All of the disclosures in this group of U.S. patents relate to test strips for detecting a liquid analyte, particularly for use in testing body fluids such as blood serum or urine.

A test strip used for titrametric analysis is disclosed in U.S. Pat. No. 3,510,263 to Hach. According to Hach, the test strip, comprising a bibulous member such as filter paper, is impregnated with a titrant and indicator. The strip is immersed into the liquid sample. A change in indicator color will occur until the end point is reached, and because the test strip is provided with a printed calibration scale for the titrant, the concentration of the test solution can be read off the printed scale. Here again, the analyte is a liquid, and the test strip is immersed into the liquid sample.

A test strip of bibulous material such as filter paper is also disclosed in U.S. Pat. No. 3,409,405 to Mohan et al. The test strip, which is used for detecting formaldehyde in body fluids, is impregnated with phenylhydrazine hydrochloride, ferric ammonium citrate, and tribasic potassium phosphate. In use, the test strip is contacted with a sample of the body fluid and with hydrochloric acid, and the presence of formaldehyde is indicated by a visible color change. Here too, the test strip is useful for liquids only, and moreover requires an exogenous reagent, i.e., hydrochloric acid, as did the above patent to Lambert et al. requiring water.

A test method utilizing a carrier with a color-change indicator for detecting a volatile substance in a liquid is disclosed in U.S. Pat. No. 4,201,548 to Tomaoku et al. In this patent, the detector comprises a composite having a cover plate provided with sample holes or wells, and a gas permeable membrane covering one surface of the plate. A carrier impregnated with a chromogenic agent is contacted with the membrane, and a second cover plate, having either observing windows or being of a transparent material, is positioned on the opposite side of the carrier. A test sample of liquid is poured into the holes, and a vaporizing agent is added to the liquid. A volatilized component of the liquid is released and permeates the membrane, and upon contact with the chromogenic reagent, produces a color change. The test apparatus is described as useful for testing liquids such as blood, urine or waste water, and for determining the presence of ammonia, amines, halogens, nitrogen oxides, and sulfur compounds. The apparatus, however, is limited to testing small liquid samples, and requires the use of an exogenous reagent, i.e., vaporizing agent.

This invention has, therefore, as its purpose to provide an analytical device, and method of using same, for detecting in situ a gaseous or volatile analyte emitted from a solid material, thereby being source specific; further requires minimal or no technical training, instrumentation, operator time, special analyses; and is convenient, transportable, rugged, and inexpensive.

SUMMARY OF THE INVENTION

Broadly, this invention provides an analytical device for detecting a gaseous or volatile analyte emitted or released from a solid material, and is adaptable to be applied directly to or in contact with a surface of the solid material. The device comprises (a) a substrate for adjacent disposition on a surface of the solid material from which the analyte is emitted, said substrate being substantially inert to the analyte, (b) an analyte-reactive component, and (c) an indicator. No exogenous reagent is utilized by the detector or in the process. When the detector is applied to the surface of the solid material, a detectable reaction occurs (e.g., color-forming reaction or signal) with the analyte emitted or released from the solid material. Because the detector is in contact with the solid material, emissions are detected or indicated from the source, per se, in contrast to detecting a volatile or gaseous analyte in ambient or atmospheric air that could have originated from any source. As stated above, the substrate is provided with an analyte-reactive component and an indicator as the test field, and although it is not intended that I be bound by an explanation of the chemical reaction(s) occurring, it is believed that the analyte-reactive component reacts with the analyte, and the indicator being present in sufficient amount results in a detectable reaction or signal (e.g., color change) in response to the reaction, thereby detecting the presence of the analyte in question. Further, it should be understood that the terms "analyte-reactive component" and "indicator" can refer to either the singular or the plural depending on the choice of reagents and the chemical reactions, and therefore more than one of either reagent may be required or desirable.

It should be understood that the substrate, per se, which is an essential member of the analytical device or detector, can be, but need not be in direct or actual contact with the solid material, because in an alternative embodiment of the analytical device, described below, a permeable membrane is provided for interjacent disposition between the substrate and the test surface. Regardless of the particular embodiment falling within the scope of the invention, analyte emitted from the test surface contacts the test field prior to blending with the ambient air, because the analytical device is in direct contact with the test surface of the solid material.

The term "solid material" as used herein and in the appended claims is intended to include both natural and synthetic materials or products, and further to include materials or products which have an appreciable volume, e.g., particle board or foam insulation, or materials or products which may be present as a film or layer, e.g. varnish or adhesive.

It will be observed that the analytical detector, and method of using the same, requires no exogenous reagent or substance. Thus, in utilizing the detector of the present invention, no reagent external to the detector is required in preparing for or conducting the analysis as, for example, adding a reagent to the test sample to volatilize the analyte, or adding a diluent, or adding water to the detector system to provide an ionized medium. As used herein and in the appended claims, exogenous reagent is intended to include not only the typical chemical reagents such as acids, bases, oxidizing or reducing agents, catalysts or inhibitors, but water as well.

Desirably the substrate comprises a planar strip formed of a material which is substantially inert to the analyte, and further is capable of holding, containing, sorbing, or otherwise being impressed with or impregnated with the reagents comprising the test field. Suitable materials useful in the present invention include papers, fabrics, and films, which can be cellulosic or synthetic, including nonwovens, or a combination thereof. Alternatively, the substrate may comprise a particulate or filament, such as alumina, glass fiber, glass beads, silica gel, or molecular sieves, which may be sorbent, and typically applied as a coating or thin layer on an inert carrier.

In alternative embodiments of the invention, the substrate is protected by means of an overlay for one or both surface areas. The overlay provided for interjacent disposition between the substrate and the solid material comprises a gas-permeable membrane. That is, the membrane is permeable to the gaseous or volatile analyte emitted from the solid material, and also should be substantially inert to the analyte and to the reagents applied to the substrate. Preferably, this interiorly disposed overlay or membrane is of substantially the same material as the substrate, and is retained in place during the test so as to protect the substrate from any surface contamination present on the solid test material. An overlay may be provided for the oppositely disposed surface, or outwardly disposed surface of the substrate, which may be paper, film or foil. Also, this outer overlay should be substantially inert with the reagents in the substrate and with the analyte, and further should be substantially impermeable to the gaseous analyte so as to protect the test field from analyte in the surrounding air. A particularly useful exterior overlay comprises an adhesive element or member, such as a tape which is transparent to the color signal. The substrate is affixed to the tacky surface of the adhesive element and within its boundary so as to provide an overlap of the tacky surface for adherence to the solid test material, and when applied to the test surface, the substrate is thereby maintained in position and protected from contamination. Desirably, the adhesive element is provided with a quick-release member, which is substantially impermeable to the analyte and protective of the detector, and is removed by the operator at the time of testing.

In conducting a test, the analytical device, for detecting in situ the gaseous or volatile emission, is placed directly onto the surface of the solid test material from which the analyte is being emitted, and in such a manner that the substrate or intervening membrane (if used) of the device is in contact with the surface of the solid material. Preferably, the detector is provided with an exteriorly-disposed overlay impermeable to the gaseous analyte so as to protect the detector from any ambient analyte. This overlay may be integral with the detector, or may be applied as a separate means for covering the detector. The gaseous or volatile analyte reacts with the analyte-reactive component, and the presence of the indicator results in a detectable reaction, e.g. color change, selective to the reaction. The particular analyte-reactive component and the concentration of this reagent applied to the substrate have been predetermined so that the moles of gaseous analyte per unit area of surface per unit of time establishes a pass or fail test. Where desired, a vacuum may be applied to the test system in order to draw the gaseous or volatile analyte from the solid material at a faster rate, thereby shortening or decreasing the test period. The color change, characteristic of the analyte emission, can be determined visually or in regions of other relevant electromagnetic spectral range, e.g., ultra-violet (UV) range.

If a more quantitative test is desired or required, an alternative embodiment provides for an analytical element with a quantitative means for determining the release of emission rate. In this art, the term "emission" has been used interchangeably with other terms of similar of the same meaning, and is used herein to include release, offgassing, degassing, desorbtion, outgassing, and the like. Thus, the substrate is produced with a concentration gradient of two or more regions of the analyte-reactive component, but with a fixed concentration of the indicator. The term "concentration" used in this context means moles of solute per unit volume of substrate. Each region is of increased concentration, and corresponds to a predetermined given concentration for the analyte. The concentration regions desirably are separated by a nonreactive zone to facilitate observation of the detectable reaction (e.g., color change). The amount of analyte emitted from the solid test surface which reacts with each of the analyte-reactive component regions of the gradient is substantially constant, but since the amount of analyte-reactive component in each of the regions increases, a visible stepwise color change is produced in the presence of a fixed concentration "lawn" of the indicator. If only a pass or fail test is required, the concentration gradient can be omitted.

An alternative embodiment provides for an analytical kit comprising the detector element and a control. Both the detector and control are made in accordance with the invention, except the analyte-reactive component is omitted from the control. The detector and control are arranged in juxtaposition on the solid test surface. A color change for the control indicates the presence of an interfering substance.

BRIEF DESCRIPTION OF THE DRAWINGS

FIG. 3 is an exploded perspective of the analytical device of FIG. 1.

FIG. 4 is a perspective view showing an alternative embodiment of the analytical device of the present invention.

DETAILED DESCRIPTION OF THE INVENTION

Figure 1:
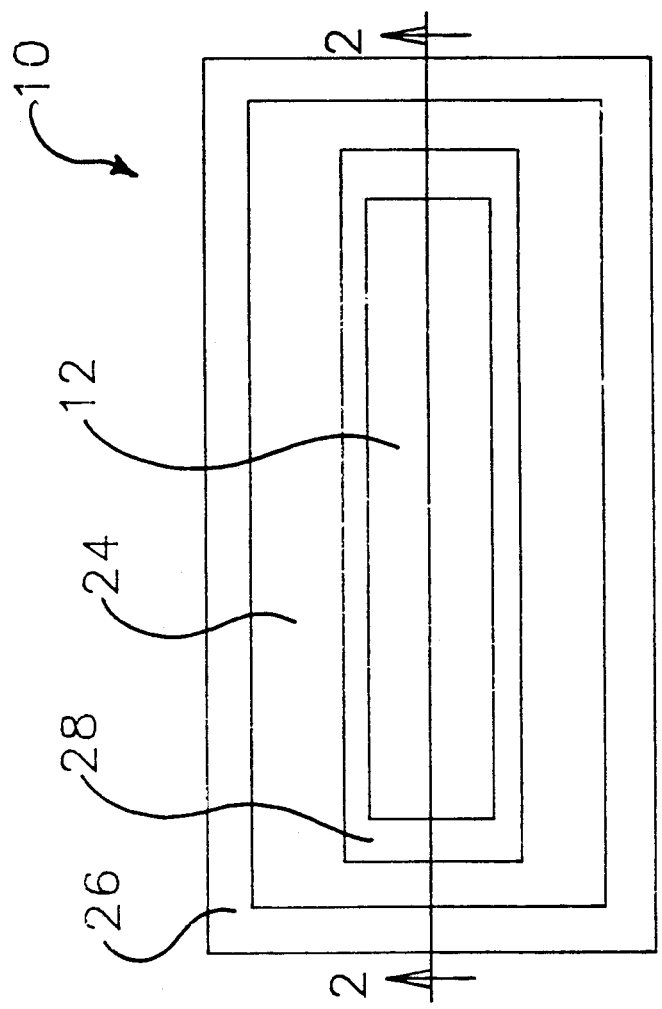
FIG. 1 is a plan view illustrating a preferred embodiment of the analytical device of the present invention.

In accordance with the present invention, there is provided an analytical device or detector for detecting the presence of a gaseous or volatile analyte emitted from a solid material. The analytical device is adaptable to be placed directly in contact with a surface of the solid test material from which the analyte is emitted, and because detection is determined in situ, the detector is source specific and detection is relatively fast and simple. These features are important because with my invention it is possible to monitor the production line of a material or product by testing that product, per se, and not a small sample of the product, or to identify the source of emissions after installation of a product rather than testing the ambient air only. That is, by using the detector of the present invention, a large, production scale (e.g., four by eight feet) panel board containing formaldehyde adhesive, for example, can be monitored for formaldehyde emissions at the production line, or similarly be tested for emissions during storage, at a converter plant, or after installation. It will be observed that the testing is non-destructive and is accomplished without prior sample preparation, or subsequent special handling and analysis. It should be understood, however, that for any analytical procedure preconditioning of the samples may be required or desirable, such as set forth in the HUD standards cited above, in order to assure that all samples have an identical pretest history. Still further, because the detector of my invention is source specific, it then is possible to monitor or identify quickly any material or product which may not meet governmental or industrial standards or may release a toxic gas to an indoor environment above a tolerable or a permissible limit.

Adverse health effects are known from formaldehyde offgassing or outgassing, and, as explained above, governmental standards have established limits for permissible amounts of emissions from manufactured products. For example, formaldehyde (which is intended to include formaldehyde derivatives such as urea formaldehyde or melamine formaldehyde) is used extensively as a resin component or adhesive in numerous wood products and building materials. Also, formaldehyde is used in several paper products to impart integrity to the web, in foam insulation, and in textiles such as permanent press fabrics or in backing, padding, or foam cushioning for carpets. Numerous other organic compounds or resins are used in such products as paints, varnishes, adhesives, etc., and there is the potential for toxic emissions after application and installation of the material. The Department of Housing and Urban Development has set standards limiting permissible amounts of formaldehyde from plywood and particle board, which emissions are not to exceed 0.2 ppm and 0.3 ppm, respectively, as measured by a specified air chamber test.

Although the invention is described with particular reference to detecting or determining formaldehyde emissions, it should be understood that the invention is also applicable to other gaseous or volatile analytes which meet the criteria of the invention, as for example, isobutane, acetone, butyl acetate, methyl acrylate, isopropyl acetate, methyl ethyl ketone, diisobutyl ketone, acetaldehyde, etc.

The analytical device includes a substrate for holding a test field of the reagent, and is disposed adjacent a surface of the solid test material so that emissions from the surface contact the test field without first blending with the ambient air. If a gas-permeable membrane is disposed interjacent the substrate test material and the analytical device, as describe below in greater detail, the substrate is not in direct contact with the test material, but as an integral composite, the detector is in direct contact. The term "adjacent" in this context is therefore understood to mean direct or near contact so that the analyte emitted from the test material to the test zone does not first blend with the ambient air. It is preferable that the substrate comprise a planar strip, such as a paper or fabric strip, because a planar strip is economical to manufacture, store, and transport, easy and economical to protect or seal from the ambient environment, easy to apply as the test material, and provides the adequate geometric area or region for holding a test field and for viewing or evaluating the test results. The substrate should be substantially inert or neutral to the analyte so as to avoid or inhibit any interference with the test reactions, and should not be influenced substantially by ambient conditions such as temperature or humidity. As explained below in greater detail, the substrate may be provided with an overlay so as to minimize or eliminate any interference or extraneous influence. Suitable substrate materials include natural and synthetic materials, such as cellulose (e.g., wood cellulose, cotton, and rayon), polyolefins (e.g., polyethylene, and polypropylene), nylon, glass fibers, and ceramic-type materials. Thus, the natural materials include paper and cloth fabric of relatively high purity, that is containing essentially no filler, loading, resin, etc., so as to avoid interfering substances; and may include, for example, high purity filter paper, which is essentially 100 percent cellulose, such as Whatman 3001-672. A natural material, e.g., paper, is particularly beneficial in that because the substrate is a major component of the detector, natural materials such as paper are biodegradable. Synthetic materials include synthetic papers, nonwoven polyolefins, glass fibers, glass beads, and such materials as silica gel, activated alumina, and molecular sieves applied as a thin coating on an inert carrier which preferably is transparent such as polyethylene tape. The substrate is of a suitable material capable of holding or containing or sorbing the reagent, such as being provided with a surface coating or impregnated coating of the reagent. In a preferred embodiment, the substrate is of a porous material so that the test field permeates the substrate, thereby making it possible to use either side as the contacting side with the solid test material, and either side for observing the test results (unless there is an interjacent membrane, described below). In a preferred embodiment, the substrate comprises a planar strip of high purity paper (e.g., Whatman 3001-672 of about 5 microns thickness) cut from a mother web or roll. Thus, the mother roll can be coated or impregnated first with the analyte-reactive component, as by spraying, dipping, brushing, spreading, printing, etc., and then dried in air or preferably in an inert or non-interfering atmosphere such as nitrogen, and/or dried in a low temperature oven of from about 25° to 90° C., which in any case may be conducted under reduced pressure, although the drying temperature can be higher depending largely on such factors as type of substrate, composition and concentration of the reagent, and drying time. The indicator coating is next applied in a similar manner. The web is then cut into individual strips, which should be of adequate length and width to provide a sufficient test field that can be easily handled and viewed by the tester. Test strips of this type can be easily protected from ambient condition, and stored in a sealed container, which is substantially impermeable to the analyte such as a polyethylene bag. Hermetic storage can be important when the detector is to be used in an area where the surrounding air contains the analyte, as for example in a manufacturing facility for pressed wood products, e.g., particle board, utilizing a formaldehyde resin.

The substrate, or at least a portion thereof, is provided with a test field comprising an analyte-reactive component or reagent. The reagent has been preselected for the particular analyte so that there takes place on the test field a chemical reaction between the reagent and analyte, and, depending upon the indicator, results in a color change or other detectable signal in the test field. The analyte-reactive component is applied to at least a portion of the substrate typically as a solution as by dipping, spraying, spreading, brushing, or printing. Depending largely upon the type of substrate and the specific reagent, a diluent, viscosity agent, dispersing agent, surfactant, or the like, may be used in the application of the analyte-reactive component to the substrate, which is within the skill of the art or may be determined by routine experimentation, and this aspect is not part of the present invention. It should be understood that depending largely on the type of substrate and physical nature of the analyte-reactive component or reagent, the substrate may be coated, impregnated, sorbed, or otherwise impressed with the reagent, and as used herein and in the appended claims, the terms "applied" or "contain" when used in this context is intended to be used in the broad sense as including any one of these techniques or similar techniques for holding the reagent.

Where desired, the analyte-reactive reagent is applied to the test field of the substrate in a substantially uniform concentration, and a pass or fail test result can be determined by the operator. If a concentration gradient is desired for a more quantitative reading (as described below in detail) with a substrate having two or more test regions, then a uniform concentration of the reagent is applied to each region and the concentration varies between regions. In this manner, and with the indicator being present in a fixed concentration, the color change or color signal will appear substantially uniformly over the entire test field or over each region of the test field. The analyte-reactive component selected is chemically compatible with the indicator so as to result in a color signal, which preferably can be determined visually or by other means such as uv light. For example, in detecting for the emissions of formaldehyde from a solid material, a particularly suitable analyte-reactive component is hydroxylamine phosphate, because it is not readily reactive with most useful substrate materials, e.g., paper, is readily soluble in water, and can be easily applied to the substrate as an aqueous solution and dried at a relatively low or moderate temperature. If one is interested in testing for acetone emissions, a suitable analyte-reactive component includes, for example, hydroxylamine hydrochloride.

An indicator, sometimes referred to as the second reactant, is incorporated into the test field of the substrate to provide a color signal, and the choice depends largely on the analyte and analyte-reactive component. The particular color signal is preselected, and preferably is in the visual range, but may be in the UV range. The indicator typically is applied to the substrate as a solution, which may be either aqueous or organic, depending on the composition of the indicator. It is desirable to apply first to the substrate the analyte-reactive component, and after adequate drying, the indicator is then applied. Here, too, the particular method of application of indicator to the substrate can be by any conventional or known means, such as by dipping, brushing, spreading, spraying, or printing, and then dried in an analyte-free or non-interfering atmosphere, e.g., nitrogen, and may be dried at an elevated temperature as in an oven, essentially as described with reference to the analyte-reactive component. Generally, this second reactant substance or indicator is applied to the substrate or test field in a manner which produces a "lawn" of uniform fixed concentration. In this manner, a substantially uniform color signal will occur over an entire test region of the substrate.

When testing a solid material containing labile formaldehyde in free or polymeric form, suitable indicators for use in conjunction with hydroxylamine phosphate include, for example Bromophenol Blue (i.e., 3,3',5,5'-tetrabromophenolsulfonphthalein), which is soluble in ethyl alcohol; or methyl orange (i.e., 4-[{(4-Dimethylanino)phenyl}azobenezenesulfonic acid sodium salt), which is soluble in water; or Bromcresol Green (i.e., 4,4'-(3H-2,1-Benzoxathiol-3-ylidene)bis[2,6-dibromo-3-methylphenol]), which is soluble in alcohol. The Bromophenol Blue is purple/blue at a pH$\geq$4, which would be the original color after application to the substrate, and yellow at a pH$\leq$3. Methyl orange has a yellow color at a pH$\geq$4.4, the original color, and red at a pH$\leq$3.1. Bromcresol Green has a blue-green color at a pH$\geq$5.4, and yellow at a pH$\leq$3.8. Although not being bound by the chemical reactions, it is believed that the key reactions are, as represented stepwise, as follows:

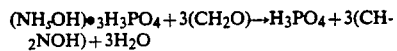

$$(NH_2OH) \cdot 3H_3PO_4 + 3(CH_2O) \rightarrow H_3PO_4 + 3(CH_2NOH) + 3H_2O$$

wherein the first mole of formaldehyde reacts completely, before the second and third moles of formaldehyde react, whereupon,

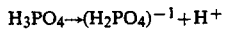

$$H_3PO_4 \rightarrow (H_2PO_4)^{-1} + H^+$$

In the presence of $H_3PO_4$ released according the above equations, the indicator Bromophenol Blue turns from purple/blue to yellow. Three moles of formaldehyde are required to react stepwise prior to the release one mole of the acid. Therefore, formaldehyde is reacted with the hydroxylamine phosphate present in the test field until completely reacted, at which point the field turns completely yellow. If the substrate is provided with a concentration gradient, then the region of the gradient with the lowest concentration of hydroxylamine phosphate turns yellow first in the presence of a given amount of formaldehyde per surface area unit, and those regions of higher concentration turn yellow more slowly, with the region of highest concentration changing to yellow last. Thus, detectors prepared with lower concentrations of analyte-reactive component are more sensitive to formaldehyde released from the test material, in that the color changes are detected at lower emission rates due to the lower concentration. Similarly, if the indicator is Methyl Orange, the color change will be from yellow to red as the reaction goes to completion within the test region; and for Bromcresol Green, the color change will be from blue-green to yellow.

In a preferred embodiment of the invention, a membrane is provided for interjacent disposition between the substrate and solid test material. The membrane is permeable to the gaseous or volatile analyte, and also is substantially inert to, or neutral with the analyte. For this particular embodiment, the membrane is in contact with the solid test material, rather than the substrate, per se, as would be the case in the absence of the membrane, and therefore the gaseous or volatile analyte in the test zone permeates the membrane and then contacts the test field of the substrate without first blending with the ambient air. It is advantageous to employ a membrane in order to protect the substrate from contamination during storage and, most significantly, from nonvolatile contaminants that may be present on the surface of the solid test material. It therefore is desirable to provide a membrane which is of essentially the same dimensions or of slightly larger dimensions than the substrate. If the membrane is of larger dimensions than the substrate, a printed calibration scale visible to the operator can be provided along one or both sides of the membrane which, when calibrated to a standard, shows the concentration gradient of analyte emitted. Also, if the dimensions of the membrane are greater than that of the substrate, the overlapping portion of the membrane can provide a section for handling by the operator without touching the test field of the substrate. In a preferred embodiment, the detector is provided with an exteriorly disposed overlay having a tacky surface or facing, which is described below in greater detail, and therefore the substrate and membrane can be joined or affixed to the tacky surface of the overlay. Any of a number of materials may be used for the membrane structure, including natural and synthetic materials, such as paper, cotton, rayon, polyolefin nonwovens, nylon, glass fiber, etc. It is preferable that the substrate and membrane are comprised of essentially the same material, and in that respect, both members can be formed of biodegradable materials, such as paper, thereby providing a composite which is essentially biodegradable.

In an alternative embodiment, there is provided an overlay of paper, film, or foil, or a combination thereof, for the oppositely disposed surface, or outwardly disposed surface, of the substrate. Suitable overlay materials include, for example, paper impregnated with a plastic to be substantially impermeable, rigid and semi-rigid polymers and/or copolymers such as Mylar (a DuPont material), polycarbonates, polyolefins, silica glass, Saran, and metal foil. This outwardly disposed overlay should be substantially inert to the reagents in the substrate and with the analyte, and further should be substantially impermeable to the gaseous analyte. In a preferred embodiment, the outwardly disposed overlay comprises an adhesive element or member, for example clear polyethylene tape, and is of sufficient dimensions so as to extend beyond the marginal edges of the substrate. In such a case, the substrate is affixed to the tacky surface of the adhesive element and within its boundary so as to provide an overlap of the tacky surface for adherence to the solid test material. If a membrane is used in the detector, as described above, it is desirable that the dimensions of the membrane be greater than that of the substrate but less than that of the outer overlay, and in that manner both the substrate and membrane can be affixed to the adhesive overlay, thereby forming a composite encapsulating the substrate and protecting it from contamination. The adhesive element should be substantially impermeable to the analyte, substantially inert to the ambient atmosphere, and optically transparent to the color signal. A particularly suitable material is, for example, clear polyethylene tape. When the adhesive element bearing the substrate is applied to the test surface, the substrate is thereby maintained in position and protected from contamination for the duration of the test. It is desirable to provide the tacky surface of the adhesive element with a quick-release member, which can be removed by the operator at the time the detector is to be utilized for the test.

Figure 2:
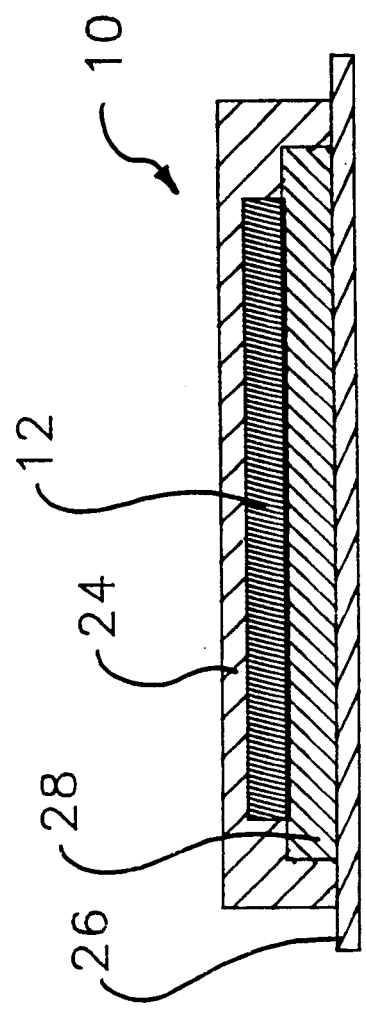
FIG. 2 is a side elevational view in cross section of the detector shown in FIG. 1 and shown on line 2—2 of FIG. 1, with dimensions exaggerated for purposes of clarity.

FIGS. 1, 2 and 3 illustrate a preferred embodiment of the invention. In the drawings, wherein like reference numerals refer to similar parts throughout the views, there is shown an analytical device or detector indicated generally by the numeral 10. The device comprises a substrate or test strip 12, desirably formed from high purity paper. The test strip may be provided with a concentration gradient in order to provide for a quantitative reading, as illustrated in FIG. 3, and includes four regions 14, 16, 18 and 20, but more or less regions can be provided depending upon the particular need. Each region is provided with a known concentration of analyte-reactive component, with region 14 having the lowest concentration and region 20 having the highest concentration. There is a fixed lawn of indicator throughout the test strip, and each test region is separated by an area 22 having indicator only. One surface of the detector (the exterior surface when in test position) is provided with an overlay 24 comprising a clear or transparent polyethylene tape, and the substrate is adhered to the tacky surface of the tape. A quick release member 26 is provided for the back surface or tacky surface of the overlay 24 to protect it until ready for use, at which time the release member is removed and the detector applied to the test surface. In an alternative embodiment, the opposite surface of the substrate is provided with a gas permeable membrane 28, also preferably of the same high purity paper as that of the substrate, for interjacent disposition between the test substrate and the solid test material. As shown, the membrane overlaps the substrate, and therefore those surfaces of the membrane extending beyond the substrate are adhered to the tacky surface of the tape. In this manner, the substrate is maintained in a secure position and is kept free of contamination. Where desired, a printed calibration scale may be provided along one side of the test strip 12, and this calibration scale may be printed onto the membrane or the overlay, or be provided as a separate strip and affixed to the overlay. In order to protect the detector from the surrounding air, the detector may be hermetically bagged for storage.

The analytical device such as of the structure shown in the drawings can be readily utilized at the test site and without the need for additional or special instrumentation. In use, the release member or backing 26 is removed, and the detector is promptly placed on the test surface of the solid material such that the outwardly extending edges of the tape 24 is affixed to the test surface. With this particular embodiment, the substrate 12 is protected by the membrane 28 from any contamination that may be present on the test surface, and by the tape 24 from any analyte present in the ambient air. If, for example, the test is for formaldehyde emissions from plywood, test region 14 would have a concentration of reagent that upon reaction with the analyte would give a color signal slightly below the permissible limit; region 16 would have a concentration of reagent that would give a color signal essentially at the permissible limit; region 18 would give color signal slightly above the limitation; and region 20 would give a color signal substantially above the limitation. Thus, from the timed interval to the color signals, the test operator would not only know if the material passed or failed, but also have a quantitative indication. It will be observed that the detector can be applied directly to the plywood panel, or any other test material, without the need for providing separate sample pieces cut from a production line panel. If desired, a suitable vacuum system, such as a vacuum cup or vacuum chamber, can be for drawing a vacuum on the test zone, thereby expediting the test. The vacuum system either should be transparent, such as of glass or plastic, or have an observation window or windows, and be provided with a proper sealing means along its marginal edges to assure an adequate seal between the vacuum means and test material.

In an alternative embodiment, the analytical detector is of sufficient dimensions to span a large section of the solid test material. A detector which spans for several feet of the breadth or length of the test material can be advantageous in that by testing a large representative surface of the test material, a more representative analysis can be achieved for a solid test material having large dimensions. Thus, the longitudinal dimension of the test strip 12 shown in FIG. 1 can be substantially equal to a dimension of the solid test material, and the test strip may have a uniform concentration of analyte-reactive component and indicator, or may be provided with a concentration gradient, as explained above. For example, in testing a 4×8 feet pressed wood panel board, the longitudinal dimension of the test strip may be substantially equal to the width of the board, and further the test strip should be of sufficient width to provide a meaningful test field. If a portion only of the test strip shows a color change, or a faster color change than other portions of the test strip, thereby indicating emissions for that area, the machine operator can be alerted that there may be a particular problem in the manufacturing process. If, for example, one side only of the test strip spanning the breadth of the panel board shows a color change, this might indicate to the operator that the pressure rollers on the production line are out of alignment.

In accordance with the embodiment shown in FIG. 4, the analytical device is provided in a substantially continuous form such as a roll, indicated generally by the numeral 32, comprising test strip 12 and adhesive overlay 24. The test strip is adhered to the tacky surface or facing of the overlay. As will be observed in the drawing, because the test strip is narrower than the overlay, when wound into a rolled form, typically on a paper or plastic core (not shown), the tacky facing of the overlay adheres to the opposed nontacky facing. In this manner, the detector is self-sealing and thereby protected from analyte in the surrounding air. Although the overlay tape 24 is of substantially continuous length, the detector strip 12 may be discontinuous, having a relatively short length (not shown), and these short strips are spaced apart from one another on the overlay backing at selected intervals or distances as required to define an individual detector of meaningful size for the particular test operation. Also, a membrane may be provided for intermediate disposition between the test strip and the surface of the solid test material. When required by the test operator, a detector may be dispensed from the roll, and a desired length is then cut from the roll. If desired, the roll may be provided with intermittent score lines in order to facilitate severing the detector from the roll.

In still another embodiment of the invention, a detector kit is provided in order to determine the validation-/invalidation of the test for the desired analyte. For the kit, a second substrate is prepared in essentially the same manner as the above described substrate with a test field, except no analyte-reactive component is applied to this second substrate. The two substrates are placed adjacent each other on the test material, such as being affixed in juxtaposition to the tacky facing of an adhesive overlay (described above) which is then applied to the surface of the solid test material. The two substrates are examined at the same time to determine if any interfering substances were present. In the event the test for the analyte is valid in that an analyte is emitted from the solid test material, the first substrate with an analyte-reactive component will render a color signal, while the control strip will not. In the case of an invalid test for the analyte in question, both substrates will change color.

The invention is further illustrated by the following examples.

EXAMPLE I

A detector was prepared by printing a test field comprising four, parallel 1.5 cm wide zones of a saturated solution of hydroxylamine phosphate (hereafter "HAP") onto a continuous roll of high purity paper measuring 10 cm in width. The paper used was chromatography paper #3001-672, Whatman Co., Hillsboro, Oreg. Printing was accomplished using a gravure press having four grooves of graduated depth, thereby applying to the paper substrate four different concentrations of HAP. These zones were separated from one another and the edges of the substrate by 8 mm intervening zones. The paper substrate was dried at room temperature in a nitrogen atmosphere free of analyte. A 0.2% wt/vol of Bromophenol Blue in ethanol as indicator was applied to the paper substrate in a manner which produced a "lawn" of uniform fixed concentration, and dried as above. Individual strips measuring one cm in width were cut from the roll, and sealed in a resealable polyethylene plastic bag or in a vacuum desiccator for storage. The test strips 12 are of a configuration substantially as shown in FIG. 1.

A single strip was taken from storage and affixed to the tacky facing of clear polyethylene tape as the overlay (polyethylene #CW-1, Manco, Inc., Westlake, Ohio). The overlay was slightly longer and wider than the paper strip, and therefore extended beyond the marginal edges of the strip. An analyte impermeable, release backer was adhered to the overlapping surface of the overlay, thereby encapsulating the paper strip. Polyethylene, glass, plexiglass, and Mylar were used as release members. Precautions were taken not to contaminate the strips.

A test was conducted on a pressed wood product (4 ft×8 ft panel) comprising a ½ inch raw backed, 2 rail vinyl faced particle board, and known to contain formaldehyde. The release backers of two detector strips were removed, and immediately affixed to the opposed surfaces of the wood panel by applying the tacky facing of the overlay to the panel surfaces. The test periods ranged from two to twelve hours. Formaldehyde emitted from the panel reacted with the HAP present in each region of the strips until completely reacted, at which point the region turned completely yellow. Regions of lowest HAP concentration turned completely yellow first, and those of successively higher HAP concentrations turned yellow more slowly. Combinations of the blue and yellow produce green as the reaction went to completion in each of the regions of the gradient. The amount of formaldehyde emitted from the test surface which reacts with HAP in the test regions of the gradient is substantially constant, but since the amount of HAP reagent in each region increases, a visible stepwise color change is produced in the presence of a fixed concentration "lawn" of the indicator. The formaldehyde released from the test surface can be calculated directly from the detector as follows:

Moles formaldehyde released = (HAP)/(3(SA)(T))

Where: (HAP = moles of hydroxylamine phosphate per surface area unit of the analyte specific reagent zone of the substrate,
(SA) = surface area of the detector zone exposed to the test surface,
(T) = time elapsed to color change.

Thus, the volume of saturated HAP applied to the substrate is calculated by multiplying 1.5 cm $\times$ 1 cm $\times$ 0.0076 cm (width of test field multiplied by the depth of the gravure printing press groove), and assuming 2 grams of HAP/100 cm$^3$, the amount of formaldehyde reacted with $1.8 \times 10^{-6}$ moles of HAP (calculated) in a given amount of time is $3.6 \times 10^{-6}$ moles/cm$^2$. The more rapid the color change, the greater the emission rate. Color changes were detected at lower or higher emission rates by using lower or higher concentrations of the analyte-reactive component.

EXAMPLE II

A detector was prepared as in Example I except that the quantity of HAP in each region of the gradient was less than that used for each region in Example I. Pressed wood products having different surface treatments were tested for formaldehyde emission. The materials tested, time of test, and emission rates are shown in the following table.

TABLE 1

Formaldehyde Emission Rates

| Ex. No. | Material | Surface Tested | Mean Emission Rate Moles CH$_2$O/cm$^2$/hr |
|---|---|---|---|
| A | Medium density fiber board | Vinyl face | $0.9 \times 10^{-7}$ |
| B | Particle board | Paper face | $1.9 \times 10^{-6}$ |
| C | Particle board | Vinyl face | $3.1 \times 10^{-7}$ |
| D | Plywood | Impregnated paper face | $4.7 \times 10^{-7}$ |
| E | Kitchen cabinet (particle board) | Vinyl face | $0.5 \times 10^{-8}$ |

It will be observed that testing with detectors prepared for this example were more sensitive to formaldehyde released, in that the color changes were detected at lower emission rates due to the lower concentrations of HAP in each of the regions of the gradient as compared to Example I.

EXAMPLE III

A detector strip, prepared substantially as in Example I, was used in conjunction with a semipermeable membrane, which was interposed between the strip and surface of the test material. The membrane was formed of the same paper as the detector strip, and was permeable to, and nonreactive with, formaldehyde. The test material was raw particle board. At the end of two hours, the first and second gradient of the detector strip changed to the yellow color, thereby demonstrating that the membrane did not interfere with the test.

EXAMPLE IV

The detector strip of Example I was used in conjunction with a control strip which contained no HAP. The two strips were applied adjacent each other on the surfaces of particle board and plywood. By including a control strip, the validation/invalidation of the test for the analyte can be determined by the operator. In the event the test is valid, the detector strip (containing HAP) would change color while the control strip would not. In the case of an invalid test for analyte, both detector and control strips would change color. After about two hours, the detector strip only showed the yellow color change, thereby demonstrating a valid test.

EXAMPLE V

A detector strip was prepared essentially as in Example I, except that a single analyte-reactive zone or region was used. In separate experiments using particle board and plywood, and conducted for about two hours, the amount of HAP ranged from about $9 \times 10^{-7}$ to $1.2 \times 10^{-5}$ moles/cm$^2$. This corresponded to formaldehyde release/emission/offgassing rate of $6.2 \times 10^{-7}$ to $8 \times 10^{-6}$ moles formaldehyde/cm$^2$/time unit.

EXAMPLE VI

The experiment of Example I was repeated, except that the test sample with the detector was placed under a partial vacuum measuring −600 mm mercury. The release rates for formaldehyde were about two and one-half times faster as compared to conducting the test at atmospheric pressure. Hence, the test period can be shortened by using this technique.

It will be observed that by reason of my invention numerous advantages are realized in detecting noxious emissions. The source of the emission, per se, can be determined, that is, the detector is source specific; there is no destruction of a the product undergoing testing; sample preparation is eliminated or greatly reduced;, and no exogenous reagents are used. Still further, no special skill or trained technician is required for conducting the test, and no second or subsequent analysis, particularly a wet analysis, is performed by an operator.

I claim:

1. An analytical device for detecting a gaseous or volatile analyte emitted in situ from a component incorporated into a solid material, said device adaptable to be applied directly to a surface of a said solid material from which said analyte is emitted, comprising: a substrate for disposition adjacent a surface of said solid material, said substrate having applied thereto (a) an analyte-reactive component which reacts with said analyte, and (b) an indicator in sufficient quantity to produce a detectable signal selective to the reaction thereby detecting said analyte; an overlay for said substrate outwardly disposed relative to said surface of said solid material, said overlay being substantially impermeable to said analyte and being substantially inert to said analyte and to said analyte-reactive component; and said analytical device requiring no exogenous reagent.

2. An analytical device according to claim 1 wherein said substrate is a planar strip.

3. An analytical device according to claim 2 wherein said planar strip is a cellulosic material which is substantially inert to said analyte.

4. An analytical device according to claim 1 wherein said substrate is a material selected from the group consisting of paper, fabric, nonwovens, film, glass fiber, glass beads, ceramic, or sorbent particulate.

5. An analytical device according to claim 1 including a membrane applied to said substrate for interjacent disposition between said substrate and said solid material, said membrane being permeable to said analyte and substantially inert to said analyte.

6. An analytical device according to claim 5 wherein said substrate and said membrane are of substantially the same material.

7. An analytical device according to claim 6 wherein said substrate and said membrane comprise paper.

8. An analytical device according to any one of claims 1-7 wherein said overlay being optically transparent to said detectable signal 9. An analytical device according to one of claims 1-7 said overlay comprises an adhesive element having a tacky facing and overlaying said substrate, said overlay having an area of said tacky facing extending beyond the marginal edges of said substrate for affixing said substrate to said surface of said solid material, said adhesive element being substantially impermeable to said analyte, being substantially inert to said analyte and to said analyte-reactive component, and optically transparent to said detectable signal.

10. An analytical device according to claim 9 including a release member overlaying said adhesive element.

11. An analytical device according to claim 10 wherein said adhesive element is polyethylene.

12. An analytical device according to claim 11 which includes said substrate having a concentration gradient of said analyte-reactive component defining a plurality of concentration regions.

13. An analytical device according to claim 12 wherein each concentration region is separated by one or more nonreactive zones.

14. A detector kit for detecting the presence of a gaseous or volatile analyte and adaptable to be applied directly to the surface of a solid material from which said analyte is emitted, comprising: a first substrate for adjacent disposition with a surface of said solid material, said first substrate having applied thereto (a) an analyte-reactive component which reacts with said analyte, and (b) an indicator in sufficient quantity to produce a detectable signal selective to the reaction thereby detecting the presence of said analyte, and said detector having no exogenous reagents; and a second substrate for adjacent disposition with a surface of said solid material, said second substrate having applied thereto the same indicator as applied to said first substrate; said first and second substrates affixed in juxtaposition to the tacky facing of an adhesive element having overlapping edges for affixing said substrates to said surface of said solid material; said adhesive element being substantially impermeable to said analyte, being substantially inert to said analyte and to said analyte-reactive component, and optically transparent to said color signal.

15. A detector kit according to claim 14 including a release member overlaying said adhesive element.

16. An analytical device for detecting the presence of gaseous or volatile formaldehyde emittable from a solid material and adaptable to be applied directly to a surface of a said solid material having incorporated therein a formaldehyde component from which the formaldehyde is emitted, comprising: a substrate for disposition adjacent a surface of said solid material, said substrate having applied thereto (a) an analyte-reactive component which reacts with formaldehyde, and (b) an indicator in sufficient quantity to produce a detectable signal selective to the reaction thereby detecting formaldehyde; an overlay for said substrate outwardly disposed relative to said surface of said solid material, said overlay being substantially impermeable to formaldehyde and being substantially inert to formaldehyde and to said analyte-reactive component; and said analytical device requiring no exogenous reagent.

17. An analytical device according to claim 16 wherein said analyte-reactive component is hydroxylamine phosphate.

18. An analytical device according to claim 17 wherein said indicator is selected from the group consisting of Bromophenol Blue, Bromcresol Green, and Methyl Orange, and the detectable signal comprises a color signal.

19. An analytical device according to claim 16 wherein said substrate comprise a cellulosic material which is substantially inert to said analyte.

20. An analytical device according to claim 19 wherein said substrate comprises paper.

21. An analytical device according to any one of claims 16, 17, 18, 19 or 20 including a membrane applied to said substrate for interjacent disposition between said substrate and said solid material, said membrane being permeable to gaseous formaldehyde and substantially inert to formaldehyde and to said analyte-reactive component.

22. An analytical device according to claim 21 wherein said membrane and said substrate are of substantially the same material.

23. An analytical device according to claim 22 wherein said membrane and said substrate comprise paper.

24. An analytical device according to any one of claims 16, 17, 18, 19, or 20, wherein said overlay comprises an adhesive element overlaying said substrate and extending beyond the marginal edges of said substrate for affixing said substrate to said surface of said solid material, said adhesive element being optically transparent to said color signal.

25. An analytical device according to claim 24 including a release member overlaying said adhesive element.

26. An analytical device according to claim 25 including a membrane applied to said substrate for interjacent disposition between said substrate and said solid material, said membrane being permeable to gaseous formaldehyde and substantially inert to formaldehyde and to said analyte-reactive component.

27. An analytical device according to claim 26 wherein said membrane and said substrate are of substantially the same material.

28. An analytical device according to claim 27 wherein said membrane and said substrate comprise paper.

29. An analytical device according to claim 1 or claim 16 which includes said substrate having a concentration gradient of said analyte-reactive component defining a plurality of concentration regions.

30. An analytical device according to claim 29 wherein each concentration region is separated by one or more nonreactive zones.

31. An analytical device for detecting the presence of gaseous or volatile formaldehyde emittable from a solid material and adaptable to be applied directly to the surface of the solid material from which the formaldehyde is emitted, comprising: a substantially planar strip of a cellulosic material for adjacent disposition with a surface of said solid material, said substrate having applied thereto (a) an analyte-reactive component which reacts with formaldehyde, and (b) an indicator in sufficient quantity to produce a color specific to the reaction thereby detecting formaldehyde; a membrane applied to said planar strip for interjacent disposition between said planar strip and said solid material, said membrane comprising a cellulosic material, and being permeable to gaseous formaldehyde and substantially inert to formaldehyde; and an adhesive element having a tacky facing overlaying said planar strip and said membrane and leaving an exposed area of said tacky facing for affixing to said surface of said solid material, said adhesive element being substantially impermeable to formaldehyde and substantially inert to formaldehyde; said analytical device having no exogenous reagent.

32. An analytical device according to claim 31 which includes said planar strip having a concentration gradient of said analyte-reactive component defining a plurality of concentration regions.

33. An analytical device according to claim 32 wherein each concentration region is separated by one or more nonreactive zones.

34. An analytical device according to any one of claims 29, 30, 31, 32 or 33, wherein said planar strip is wound into a roll form.

35. A method for detecting the presence of a gaseous or volatile analyte emitted from a solid material, which comprises providing a substrate having (a) an analyte-reactive component which reacts with said analyte, and (b) an indicator in sufficient quantity to produce a color specific to the reaction thereby detecting the presence of said analyte, placing said substrate adjacent a surface of said solid material, providing an overlay for said substrate, said overlay being substantially impermeable to said analyte, allowing sufficient time for said reaction to occur, and observing any change in color on said substrate.

36. A method according to claim 35 and further including providing a substrate comprising a cellulosic planar strip containing hydroxylamine phosphate as the analyte-reactive component and Bromophenol Blue as the indicator.

* * * * *